United States Patent [19]
Fangrow, Jr. et al.

[11] Patent Number: 5,839,436
[45] Date of Patent: Nov. 24, 1998

[54] DEMAND VALVE WITH A REDUCED MANUAL FLOW CONTROL

[75] Inventors: Thomas F. Fangrow, Jr., Corona; Donald G. Rulifson, Yorba Linda, both of Calif.

[73] Assignee: Life Support Products, Inc., Irvine, Calif.

[21] Appl. No.: 512,129

[22] Filed: Aug. 7, 1995

Related U.S. Application Data

[63] Continuation of Ser. No. 943,781, Sep. 11, 1992, abandoned.

[51] Int. Cl.⁶ .............................. A62B 9/02; A62B 7/04; F16K 31/26
[52] U.S. Cl. .............................. 128/205.24; 128/204.26; 128/204.18; 128/207.12
[58] Field of Search .................. 128/201.28, 203.11, 128/204.18, 204.26, 205.11, 205.13, 205.24, 205.25, 207.12

[56] References Cited

U.S. PATENT DOCUMENTS

| | | | |
|---|---|---|---|
| 3,795,257 | 3/1974 | Fabish et al. | 137/491 |
| 3,978,854 | 9/1976 | Mills, Jr. | 128/204.26 |
| 3,991,785 | 11/1976 | Trinkwalder, Jr. | 128/204.26 |
| 3,995,625 | 12/1976 | Needham | 128/204.26 |
| 4,111,197 | 9/1978 | Warncke et al. | 128/204.26 |
| 4,121,580 | 10/1978 | Fabish | 128/205.24 |
| 4,207,884 | 6/1980 | Isaacson | 128/200.24 |
| 4,274,404 | 6/1981 | Molzan et al. | 128/204.25 |
| 4,374,521 | 2/1983 | Nelson et al. | 128/205.13 |
| 4,378,795 | 4/1983 | Feathers et al. | 128/202.27 |
| 4,606,340 | 8/1986 | Ansite | 128/205.24 |

Primary Examiner—Kimberly L. Asher
Attorney, Agent, or Firm—Dickstein Shapiro Morin & Oshinsky LLP

[57] ABSTRACT

A demand valve resuscitator having a reduced manual flow control. The resuscitator connects between a source of pressurized gas and a breathing mask. A patient may draw a flow of gas on demand through the resuscitator by inhaling. A pressure-responsive diaphragm within a pressure chamber, actuated on demand or manually, acts on a tilt valve in a gas intake port. Alternatively, an attendant may supply a reduced flow of gas to a patient by depressing a manual control button, which tilts the intake valve. The manual control of the gas flow is overridden by excess pressure within the pressure chamber of the resuscitator and the button must be released to reassert manual control. A baffle plate in the pressure chamber provides a venturi assist to reduce pressure adjacent the diaphragm to enable the patient to obtain maximum gas flow on demand with slight inhale suction. An anti-suffocation valve allows the patient to breath ambient air in the absence of a predetermined gas inlet pressure. The anti-suffocation valve is disposed in an intake assembly having an inlet fitting capable of swiveling without affecting the operation of the tilt valve.

18 Claims, 9 Drawing Sheets

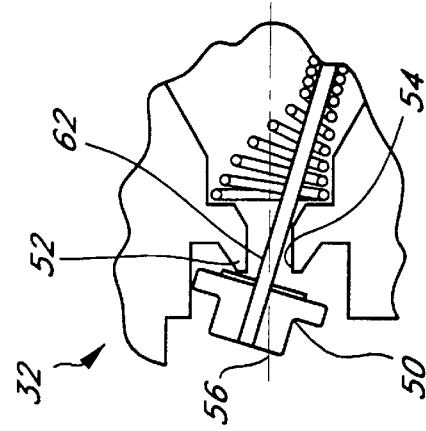
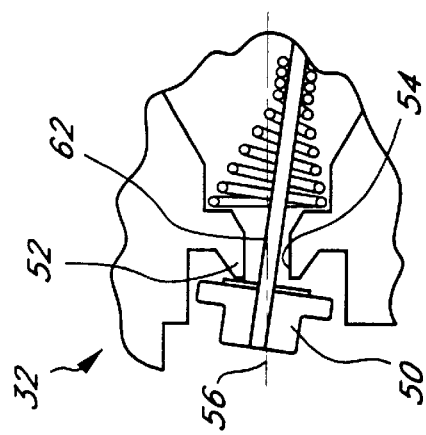
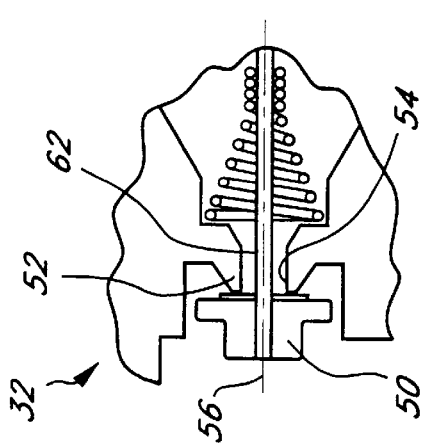
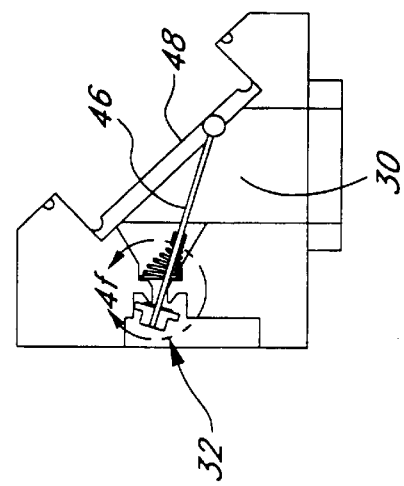
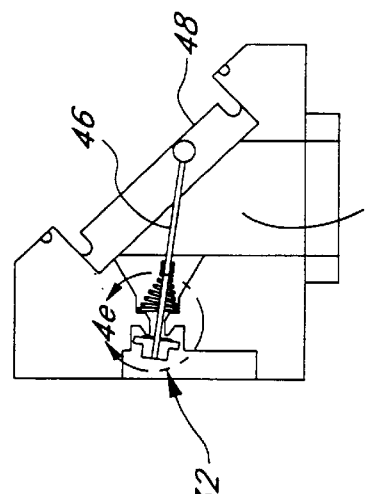
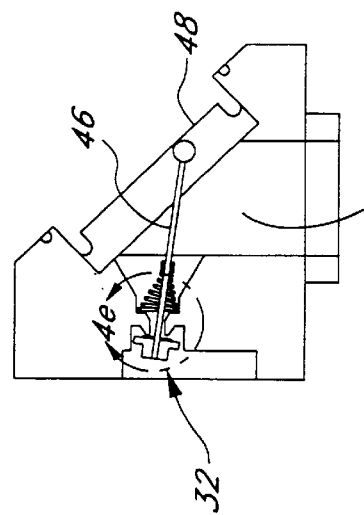
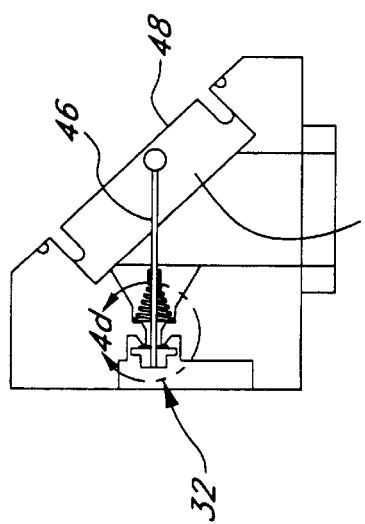

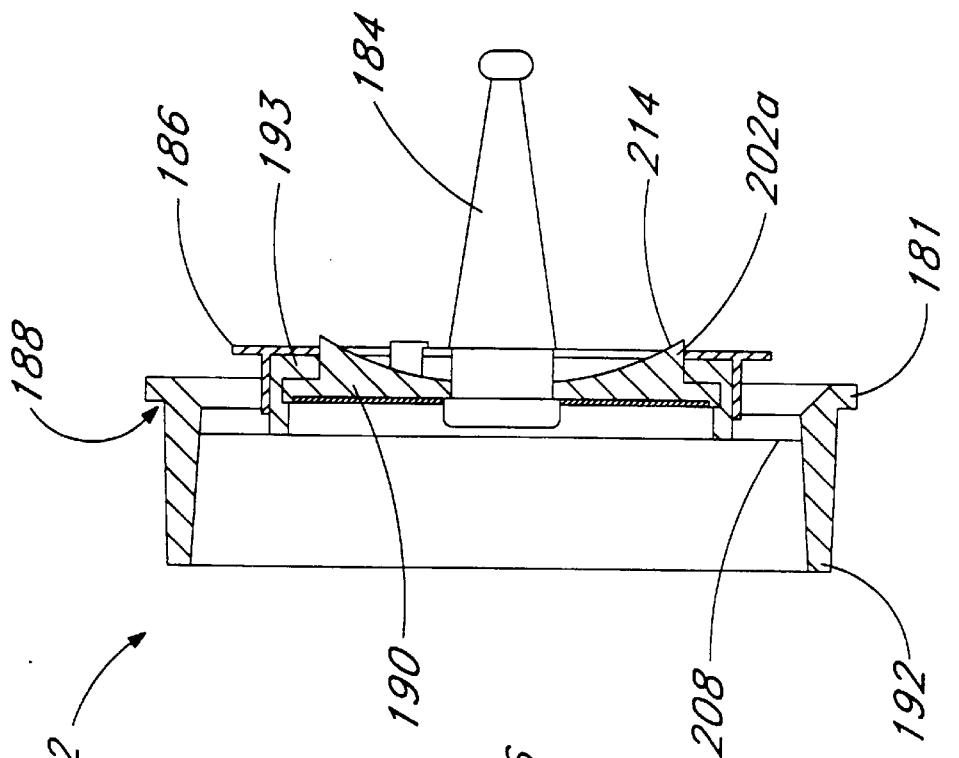
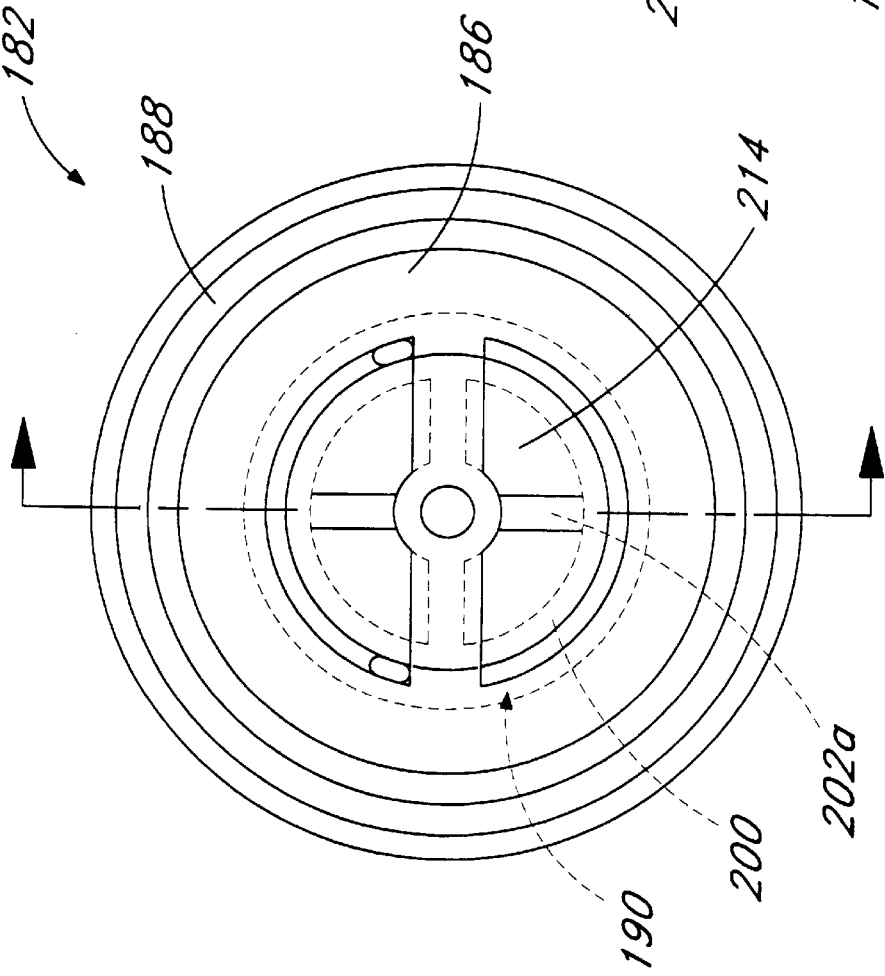
FIG. 6b
FIG. 6a

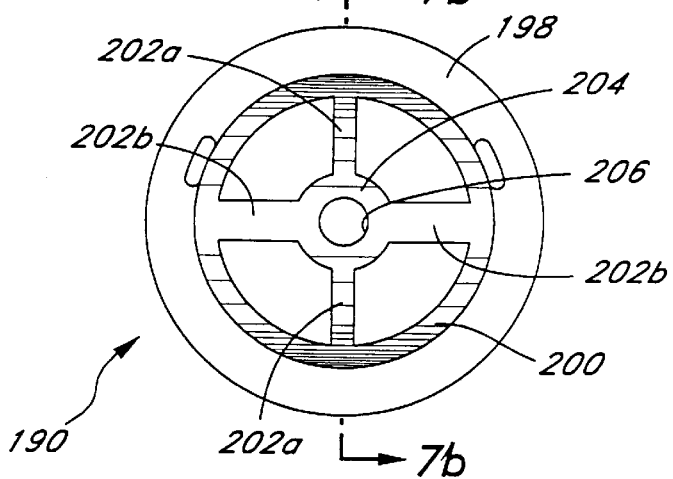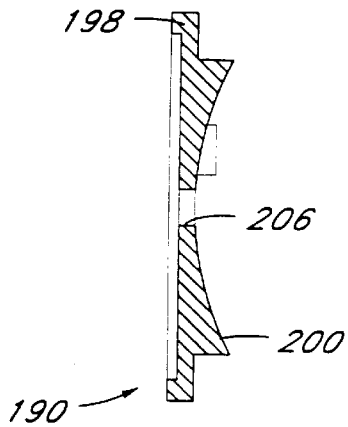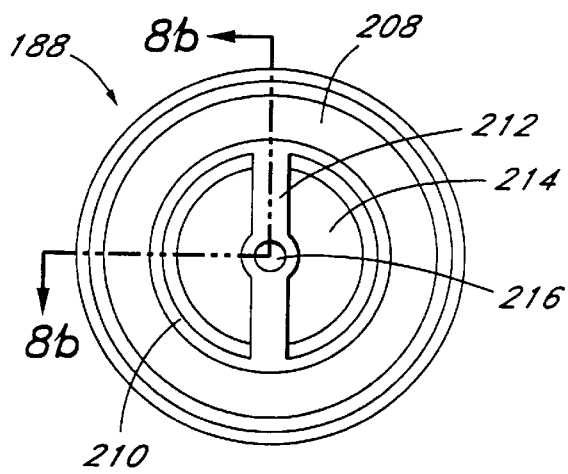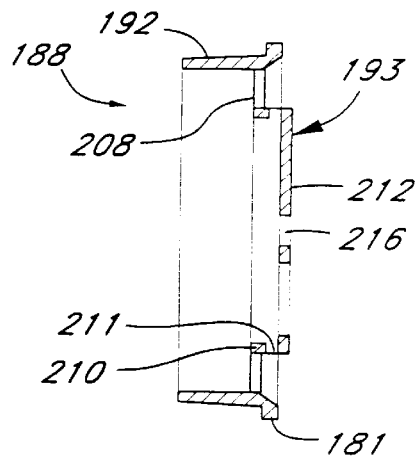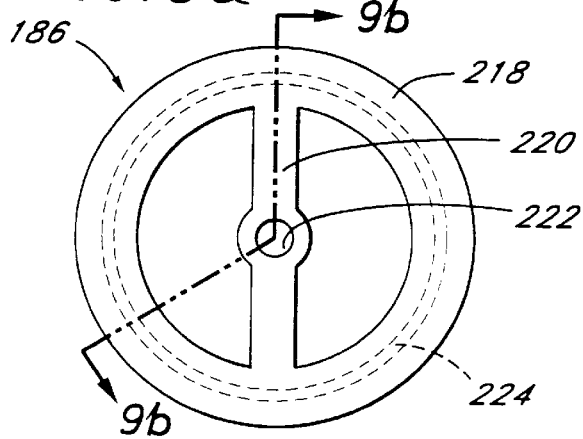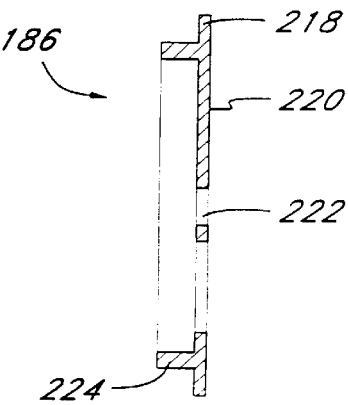

DEMAND VALVE WITH A REDUCED MANUAL FLOW CONTROL

This application is a continuation of U.S. patent application Ser. No. 07/943/781, filed Sep. 11, 1992, now abandoned.

FIELD OF THE INVENTION

The present invention relates to a demand valve for use with breathing or resuscitation equipment, and more particularly to a valve apparatus with an improved manual flow control.

BACKGROUND OF THE INVENTION

Demand valves in general regulate gas flow such as oxygen into a closed system such as an emergency breathing system, aircraft oxygen system, resuscitator and the like. Demand valves are typically installed between a source of oxygen and a breathing mask so that the patient can obtain oxygen "on demand", or when inhaling. Typically, the patient inhales to produce a negative pressure within a chamber of the demand valve to pull a diaphragm and open a valve, starting the flow of oxygen. It is not uncommon for the patient to have stopped breathing. Various devices have been combined with the demand valve to provide the operator with manual override, allowing the operator to inject oxygen, or effectively breathe for the patient prior to the patient regaining normal breathing.

Numerous devices incorporating squeeze bags or manual flow control buttons are known. In emergency resuscitators, the paramedic manually delivers intermittent bursts of oxygen until the patient can breathe normally and actuate the oxygen flow "on demand." Until the patient regains regular breathing, however, exhalation through the demand valve is only accomplished by the muscles of the patient's lungs contracting. Occasionally, the patient may need to exhale while oxygen is being delivered, or the patient's lungs may have reached capacity. During the manual introduction of oxygen, the patient may be unable to exhale or to prevent further oxygen inflow, if the demand valve is not sensitive to certain feedback pressure.

Presently, demand valves include an oxygen delivery valve which flows unobstructed into a pressure chamber. The patient must create a suction within the pressure chamber to initiate the flow of oxygen which entry then tends to counteract the reduced pressure within the chamber or, in some cases, acts directly on the actuating diaphragm to force it in a direction to enlarge the chamber. The patient must then overcome these dynamic changes by inhaling that much harder to receive maximum flow. It would be preferable to allow the patient to more easily obtain the maximum possible oxygen flow.

Many current demand valves include some sort of bypass to prevent suffocation of the patient when the oxygen supply is either blocked or runs out. Such a situation may occur, for example, by operator negligence if the patient is left alone for a moment and the oxygen runs out, or, if the oxygen gauge is faulty. It is desirable that such a bypass incorporated into the demand valve allows the patient to breath ambient air with a minimum of effort when the oxygen supply stops.

Current demand valves permit the same flow rate during both demand and manual control operation. In the past, it was widely assumed that the patient required the same amount of oxygen when normally breathing as when oxygen was administered manually. It was believed that the more oxygen delivered, the greater the chances of recovery were. Recently, however, the medical profession has recognized that a reduced flow during manually-assisted breathing is preferred to avoid forcing oxygen into the patient's stomach and other complications. However, the operator of the known valves cannot accurately regulate a reduced flow of oxygen to the patient by partially actuating the manual control. Typically, prior controls have been too sensitive to enable manual metering of oxygen effectively. And unfortunately, simply restricting the maximum flow allowable prevents the patient from receiving a desired increased flow during demand operation.

A further characteristic of demand valves of the prior art has been a difficulty in conforming to the various angles or attitudes at which the patient lies. Specifically, the hoses typically used between the oxygen tank and the breathing mask and demand valve are somewhat rigid. The rigidity of the supply hose can adversely affect the exact positioning of the breathing mask over the patient's mouth. Also, the hose should not affect the operation of the demand valve.

Various demand valves are shown in the prior art, one of which, U.S. Pat. No. 3,978,854 to Mills, Jr., discloses a demand regulator which utilizes a diaphragm-actuated tilt valve to supply oxygen to the patient. The diaphragm moves in response to a slight pressure differential across its opposing faces. In one embodiment, a manual actuator is added. U.S. Pat. No. 3,795,257 to Fabish, et al. also shows a demand valve with a manual control button. Both the patents to Mills and Fabish include a manual control override responsive to excessive back pressure on the patient's side of the diaphragm. Both manual controls are provided with independently slidable inner members spring biased against the manual control side of the diaphragm. Patient exhalation pressure forces the diaphragm against the bias of the spring to eventually shut off the flow of oxygen. However, maintaining pressure on the manual control button will also maintain pressure against the diaphragm, via the spring and sliding member, against the patient's exhalation pressure. Thus, the force of the patient's exhalation against the diaphragm is required continuously for a short time until the diaphragm closes off the oxygen supply. The initial exhalation work done by the patient can be insufficient to shut off the oxygen flow if not maintained. Furthermore, the exhalation path of the device of Mills includes a flapper valve in the diaphragm itself. The slidable member of the manual control exerts a force against the flapper valve and diaphragm, making it more difficult for the patient to exhale, regardless of the level of exhalation pressure.

Various devices to allow a patient to breathe when an oxygen supply is restricted are shown. U.S. Pat. No. 4,274,404 to Molzan, et al. shows an oxygen supply system which includes a flapper valve enabling the patient to inhale atmospheric air when the oxygen supply is turned off. However, the patient may also inhale atmospheric air through the flapper valve when the flow of oxygen is on as well, providing a mixture of oxygen and air. U.S. Pat. No. 4,374,521 to Nelson, et al. discloses a squeeze bag resuscitator which includes a contingency pathway for air to enter the squeeze bag in the event of the oxygen flow being depleted. In U.S. Pat. Nos. 4,606,340 to Ansite and 4,121,580 to Fabish, breathing valves with anti-suffocation means are shown. Both the Ansite and Fabish devices, however, require the patient to overcome resilient springs or flapper valves prior to inhaling air freely.

Thus, there is a need for an improved demand valve with manual flow control which overcomes the above mentioned aspects of the prior art.

SUMMARY OF THE INVENTION

The present invention provides a resuscitator for supplying breathing gas to a patient, generally comprising a housing having a pressure chamber with a breathing gas inlet and a breathing gas outlet for directing gas from the chamber to a patient. A normally closed valve in the inlet for controlling the flow of breathing gas into the chamber, is movable into an open position in response to negative pressure in the chamber caused by a patient's inhalation demand for breathing gas due to the movement of a pressure responsive element in the chamber, such as a flexible diaphragm. Alternatively, a manually-controlled actuator may move the diaphragm in a manner to open the valve. However, the actuator is responsive to a predetermined threshold pressure in the chamber applied to the diaphragm to become temporarily unable to move the diaphragm. Thus, manual flow is limited to a predetermined maximum, less than maximum demand, but maximum manual flow can be maintained until the control is abruptly disabled. In accordance with a preferred embodiment, the actuator movement opening the valve is limited to provide about one-third of the flow that the valve can provide in response to patient demand.

The inlet valve of the resuscitator preferably includes a slender elongated valve stem that extends into the chamber, the diaphragm being positioned close to a free end of the valve stem. The diaphragm is oriented such that a reduction in pressure in the chamber caused by the patient demanding breathing gas will cause the diaphragm to move the valve stem so as to open the valve. The actuator similarly moves the diaphragm in a direction to move the end of the valve stem so as to open the valve.

The actuator preferably includes an actuator pin positioned to push the pressure-responsive diaphragm towards the valve stem, and a manually operated control button connected to the actuator pin by a releasable detent. The detent is constructed to disable the connection between the actuator pin and the push button due to a retracting force on the pin by the diaphragm as a result of a predetermined pressure level in the chamber. The detent includes a spring-loaded pin having a tip which interconnects with the actuator pin such that when the push button is depressed, the detent pin moves the actuator pin in a direction to move the diaphragm. The disabling of the connection between the actuator pin and the push button occurs due to a predetermined force on the actuator pin causing the detent pin to retract so that it no longer connects with the actuator pin, thereby allowing the actuator pin and the diaphragm to be retracted.

In a preferred form, the actuator includes a push button positioned on one side of a partition wall, a plurality of spaced legs connected to the push button and extending through the partition, a disk connected to the legs, the actuator pin positioned being within a central opening of the connector disk, the spring-loaded detent mounted in the connector disk with its radially inner end urged into driving engagement with the pin, and a spring urging the push button into an undepressed position and thereby urging the connector disk towards the partition. The push button, together with the connector disk and actuator pin, is depressible to move the pressure responsive diaphragm to open the valve. With the push button in its depressed condition, a space develops between the actuator pin and the partition so that an increase of pressure within the chamber beyond a predetermined maximum will cause the actuator pin to be pushed towards the partition disconnecting it from the detent pin, even though the push button is still depressed. The detent pin is reconnectable with the actuator pin when the push button is manually released and moved with the connector disk to an undepressed condition by the push button spring.

In another aspect of the invention, a baffle is positioned in the pressure chamber to direct inlet oxygen flow in a manner to produce a venturi action in the chamber that cause the diaphragm to move in a direction to increase flow. This enables a patient to obtain maximum flow with a minimum of inhalation effort.

Preferably, the resuscitator includes a conduit in a wall of the resuscitator housing having one end opening into the chamber and another end adapted to be connected to a patient's breathing mask. An exhaust valve member covers the end of the conduit opening to the chamber, and a flexible diaphragm connects the periphery of the valve member to the housing. The diaphragm permits the valve member to be moved away from the end of the conduit in response to patient exhalation pressure to permit a patient to exhale through the conduit. To allow for exhalation, the housing includes an opening to the atmosphere that is in communication with the conduit when the valve member is moved away from the end of the conduit. Additionally, the exhalation valve member includes an opening for permitting breathing gas to flow from the chamber through the conduit to the patient. A one-way valve element mounted on the member covers the opening to permit gas flow from the chamber to the conduit with a very slight inhalation pressure, but prevents patient exhalation gas flow from the conduit into the chamber.

Preferably, the resuscitator includes a breathing gas inlet conduit in the housing, opening to the pressure chamber, with an inlet valve assembly positioned in the inlet conduit and including a valve stem which extends into the chamber.

The inlet valve assembly preferably includes a valve seat member positioned in the inlet conduit adjacent the pressure chamber, and a breathing gas intake fitting positioned in the conduit and capturing the valve seat within the conduit. The fitting is axially fixed within the inlet conduit but is readily removable from the conduit and rotatable therein without disturbing the inlet valve assembly. The valve seat member is generally circular and forms a valve seat for an anti-suffocation valve. The valve seat member has a central opening for the inlet oxygen flow, and one or more surrounding openings for atmospheric gas flow.

The valve assembly further includes a tubular anti-suffocation valve element having an inner end which cooperates with the anti-suffocation valve seat. A spring urges the anti-suffocation valve element away from the anti-suffocation valve seat such that the valve element is in a normally open position. The inlet conduit has a vent which completes a passage from the exterior of the housing through the anti-suffocation valve into the chamber to the patient gas outlet. The anti-suffocation valve element includes a surface exposed to inlet breathing gas pressure which urges the element into valve closed position in opposition to the spring whereby the anti-suffocation valve is closed when pressurized breathing gas is being supplied to the chamber but is normally open in the absence of inlet gas pressure, whereby the patient can breath through the anti-suffocation valve in the absence of adequate pressurized breathing gas input.

In a preferred method of supplying breathing gas to a patient, breathing gas is directed to a pressure chamber through a gas inlet valve which is openable in response to movement of an element, such as a flexible diaphragm, which is exposed to the pressure in the chamber. The breathing gas is directed from the chamber to a patient. The inlet valve is opened to allow gas flow into the chamber in response to movement of the diaphragm, and, in turn, in response to patient inhalation pressure. The diaphragm is also manually moved in a direction to open the inlet valve to cause gas to flow into the chamber and thereby provide gas flow to the patient when patient breathing is not adequate. The diaphragm is released from manual control when the pressure in the chamber reaches a predetermined maximum so that gas will only be supplied to the chamber in response to patient demand, or when the button is released to reset.

Manual movement of the actuating element is limited so that the flow of breathing gas under manual control can only be considerably less than the maximum that may be provided in response to patient demand. Preferably, the manually controlled flow of gas to the patient is limited to a maximum of about a third that which may be supplied in response to patient demand.

The preferred method includes utilizing the above mentioned baffle to provide venturi assisted movement of the diaphragm for ease of obtaining maximum oxygen flow on demand.

The preferred method further includes the steps of providing an anti-suffocation valve in combination with the breathing gas inlet valve; closing the anti-suffocation valve in response to the pressure of the breathing gas supplied to the inlet valve; and automatically opening the anti-suffocation valve when the breathing gas inlet pressure is below a predetermined level insufficient to provide the desired gas flow to the patient. The anti-suffocation valve when opened allows atmospheric communication to the patient through the inlet valve and the pressure chamber.

In another feature of the invention, a breathing gas inlet fitting is connected to the inlet valve in a manner that enables the fitting to rotate without affecting the inlet valve. This is advantageous in that it allows the inlet valve assembly to be tested and adjusted before installation.

BRIEF DESCRIPTION OF THE DRAWINGS

FIG. 3b is an exploded perspective view of the manual flow control button shown in FIG. 3a.

FIGS. 4a–c are schematic representations of the operation of the tilt valve within the demand valve of FIG. 1.

FIGS. 4d–f are detailed views of the valve seat portion of FIGS. 4a–c, respectively.

FIG. 5b is an isolated plan view of the oxygen flow baffle of FIG. 5a.

FIG. 6a is an isolated assembled plan view of the oxygen outlet of FIG. 5a.

FIG. 6b is a cross-sectional view of the oxygen outlet taken along line 6b—6b of FIG. 6a.

FIG. 7a is an isolated plan view of a flapper valve seat of the oxygen outlet of FIG. 6.

FIG. 7b is a cross-sectional view of the flapper valve seat taken along line 7b—7b of FIG. 7a.

FIG. 8a is an isolated plan view of an exhalation diaphragm of the oxygen outlet of FIG. 6.

FIG. 8b is a cross-sectional view of the diaphragm taken along line 8b—8b of FIG. 8a.

FIG. 9a is an isolated plan view of an exhalation valve seat of the oxygen outlet of FIG. 6.

FIG. 9b is a cross-sectional view of the exhalation valve seat taken along line 9b—9b of FIG. 9a.

FIG. 10a is a partial elevational side view of the oxygen intake of the demand valve of FIGS. 1 and 5a.

DETAILED DESCRIPTION OF THE INVENTION

Figure 1:
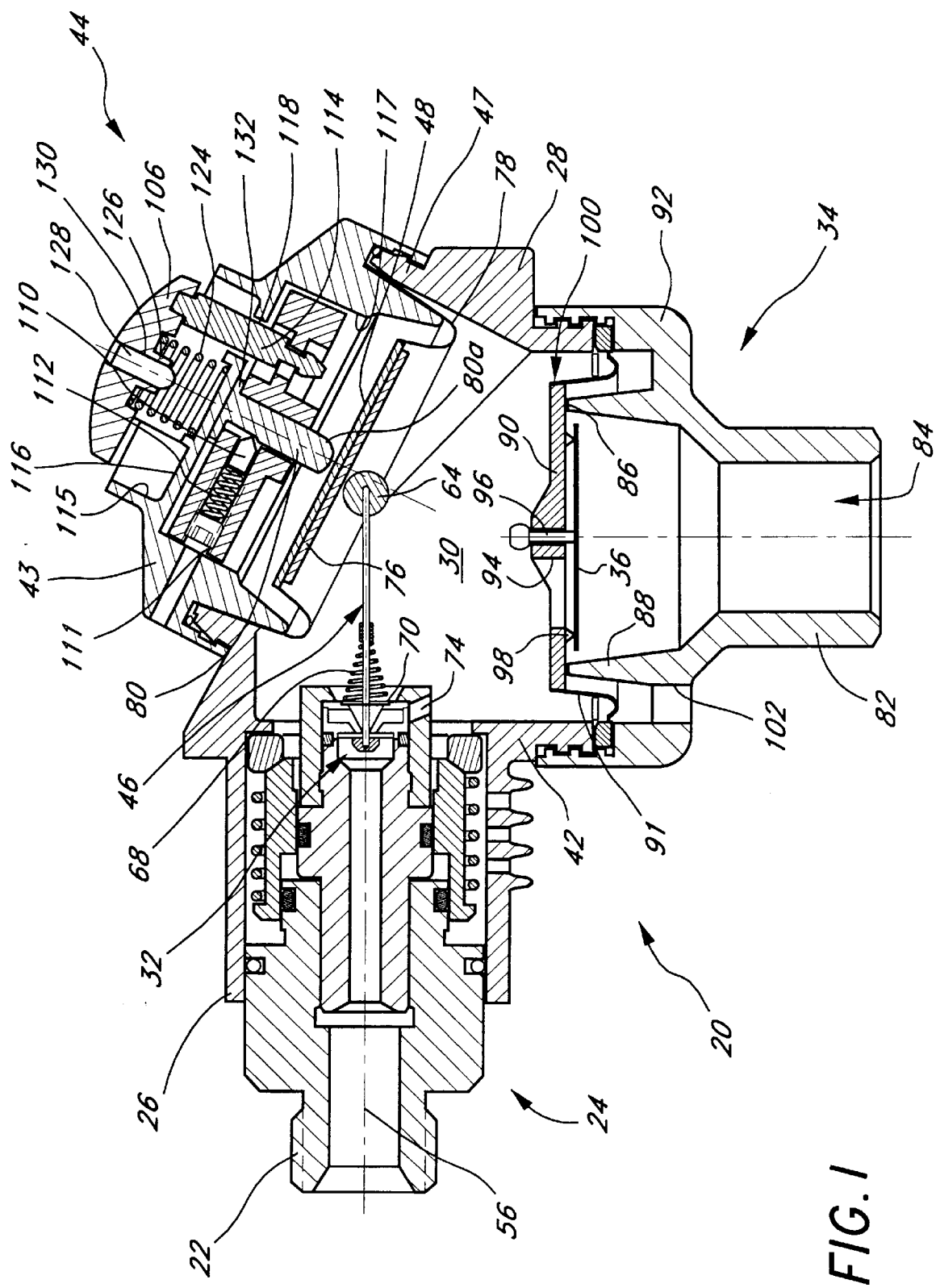
FIG. 1 is a cross-sectional view of the demand valve with reduced manual flow control of the present invention.

The demand valve 20, as shown in FIG. 1, is used primarily in emergency medical situations by paramedics as an element in a resuscitation system. A breathing gas (typically oxygen) supply hose (not shown) attaches to an intake fitting 22 at the external end of an intake assembly 24. The intake assembly mounts within a conduit 26 as an extension of a housing 28 of the demand valve. Oxygen through the fitting 22 communicates with a pressure chamber 30 within the housing 28 via a delivery valve 32. A breathing mask (not shown) mounted to an outlet port assembly 34 (170 in FIG. 5a) allows a patient to breathe oxygen from the pressure chamber 30 past a circular one-way flapper 36. When the delivery valve 32 is opened manually, oxygen flows through the pressure chamber 30 and flapper 36 to the patient through the breathing mask, filling the patient's lungs. On the other hand, the patient may inhale, causing the flapper 36 to retract and the delivery valve 32 to open, as will be described below, and thus receive oxygen "on demand."

The demand valve housing 28 generally comprises a rigid frame defining the pressure chamber 30 within and providing three mounting apertures for oxygen through-flow and control. The demand valve housing 28 and attached component are preferably non-magnetic to be compatible with medical equipment utilizing magnetic fields, waterproof to prevent corrosion and preferably constructed with a minimum of small sized parts or apertures to better resist corrosion and the effects of contamination from foreign material. Minimizing small parts also facilitates steam or chemical sterilization. The demand valve housing 28 includes the aforementioned intake conduit 26 and a shorter cylindrical outlet flange 42 for receiving the outlet port assembly 34. The flange 42 is disposed at right angles to the inlet conduit 26. A button support body 43 of a manual control button assembly 44 attaches over a circular flange 47, defining the third aperture in the housing 28. The flange 47 is oriented at an angle between the intake and outlet flanges 26, 42. The pressure chamber 30 is thus bounded on two perpendicular sides by the intake assembly 24 and outlet assembly 34 and on a third diagonal side by the control button assembly 44.

The manual control button assembly 44 is advantageously angled so as to actuate a delivery valve needle or stem 46 extending along the axis 56 of the intake assembly 24 into the pressure chamber 30. The control button 44 acts on a main diaphragm 48 which, in turn, contacts and tilts the valve needle 46 to commence a flow of oxygen through the delivery valve 32.

Figure 2A:
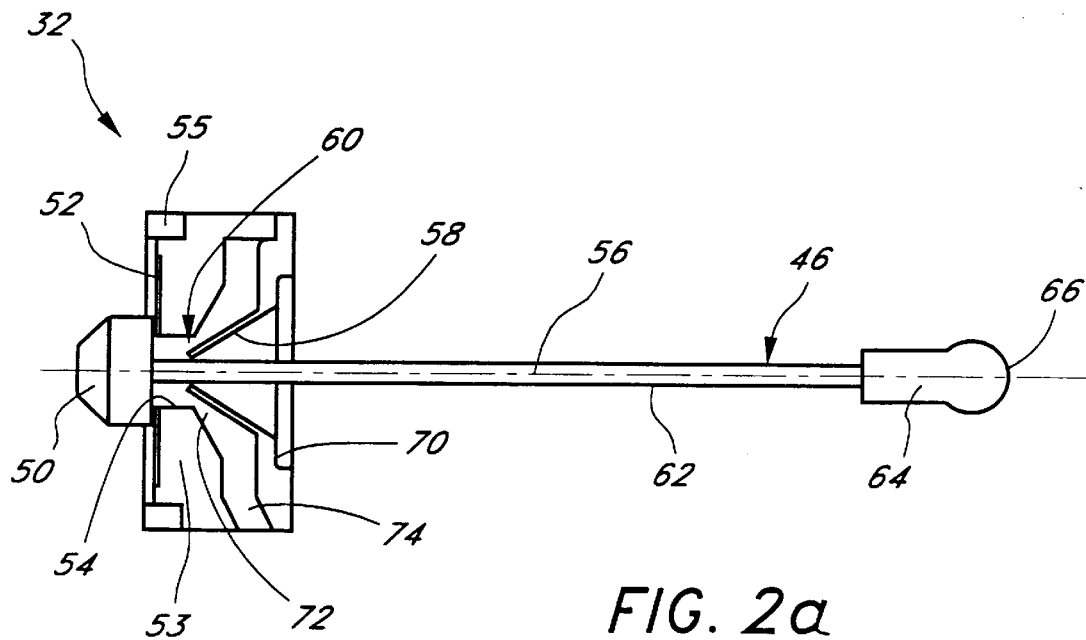
FIG. 2a is an isolated detail of the tilt valve of the demand valve of FIG. 1 in the closed position.
Figure 2B:
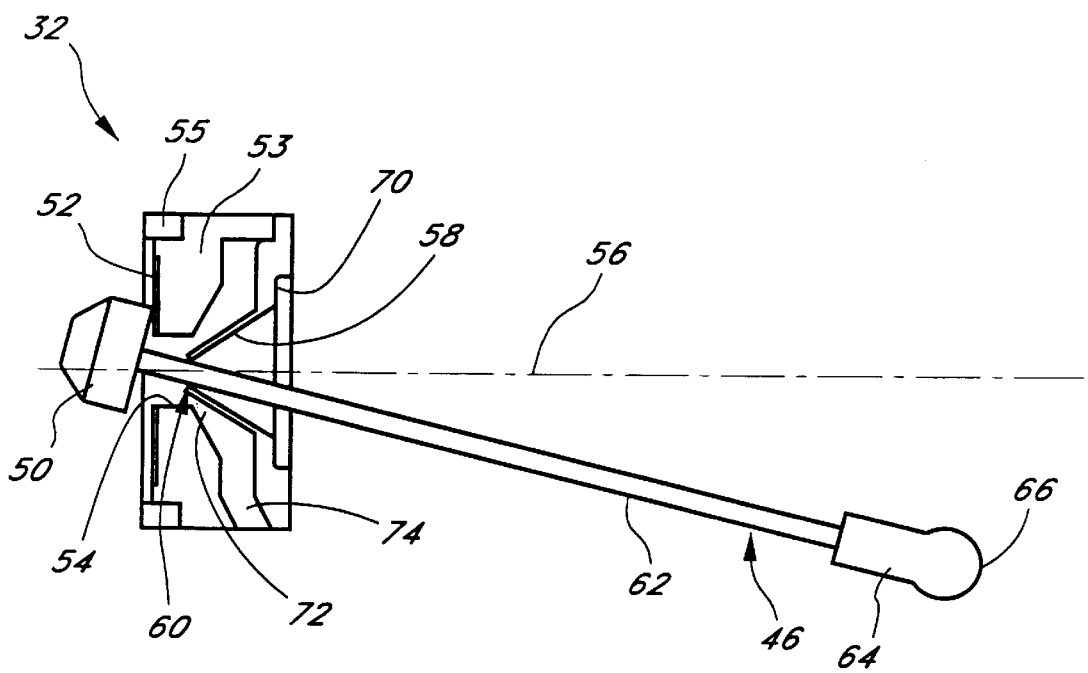
FIG. 2b is an isolated close-up of the tilt valve of the demand valve of FIG. 1 in the open position.

As shown in FIGS. 2a–b, the valve needle 46 includes a head portion 50 which rests on an elastomeric valve seal 52, molded into a recess of a preferably metallic valve seat 53, to cover an oxygen delivery port 54. The upstream (to the left) inlet oxygen pressure forces the head 50 flush against the seal 52 when the valve needle 46 is in its untilted state. The oxygen pressure on the upstream side of the head 50 also assists in returning the valve needle 46 to its horizontal state in line with the axis 56 of the intake assembly 24. A thin-walled cone-shaped deflector 58 centers the valve needle 46 about the axis 56 of the intake assembly 24, and also provides a pivot for the valve needle. The pivot point 60 is proximate the head 50 along an elongated stem 62 which extends into the pressure chamber 30. A bumper tip 64 having a rounded end 66 mounts to the distal end of the stem 62 within the pressure chamber 30 and provides a blunt contact surface for the main diaphragm 48.

The main diaphragm thus acts downwardly on the blunt tip 64 of the valve needle 46, causing the needle to pivot about the conical deflector 58. Upon pivoting of the valve needle 46, the head 50 separates from one side of the seal 52, allowing oxygen to flow to the pressure chamber 30 and then through the outlet port 34 to the patient. As shown in FIG. 1, a tapered return spring 68 mounted on its wide end to a recess of a flange 70 of the conical deflector 58, and located concentrically around the stem 62 serves to bias the needle 46 to a horizontal position, thus seating the head 50 and shutting off the flow of oxygen.

Increasing the angle at which the valve needle 46 is pivoted further increases the oxygen flow rate, as shown schematically in sequence in FIGS. 4a–f. The delivery valve 32 shown in FIGS. 4a–f is slightly different than the preferred embodiment as shown in FIGS. 2a–b; however, the concept of increasing the flow rate by increasing the tilt of the valve needle 46 remains the same. As shown in FIGS. 4a and 4d, the main diaphragm 48 does not contact the blunt tip 64 of the valve needle 46, and thus the valve needle is exactly aligned with the axis 56 of the intake assembly 24, and the valve needle head 50 positively contacts the valve seal 52. FIGS. 4b and 4e show the main diaphragm 48 advanced slightly into the pressure chamber 30 and into contact with the blunt tip 64 of the valve needle 46. The valve head 50 thus disengages from a portion of the valve seal 52, exposing the delivery port 54, and thus leaving a gap through which oxygen may flow. Further advancement of the main diaphragm 48 causes the valve needle 46 to tilt even further and widen the delivery port 54, as in FIGS. 4c and 4f.

The main diaphragm 48 may be moved in two ways. If the patient is not breathing, a paramedic presses the control button 44 to start the flow of oxygen. Alternatively, if the patient is capable of inhalation, suction generated by the patient within the pressure chamber 30 pulls the diaphragm 48 down and starts the flow of oxygen. In these two cases, direct contact pressure from an actuation shaft 80 of the control button 44, or sufficient suction within the pressure chamber 30 to deform the flexible skirt 78 inward, causes the diaphragm 48 to move into contact with the valve needle 46. The main diaphragm generally comprises a rigid plate 76 adhered to a flexible skirt 78 which extends between the housing 28 and the body 43 of the manual control button 44. The skirt 78 is sealed between the housing 28 and the manual flow control button 44 so as to provide an air-tight seal around the flange 47 into which the manual control button is secured. Preferably, the diaphragm 48 is fabricated from a silicon rubber which can withstand hostile sterilization environments and remain flexible under severe temperature extremes.

Manual Flow Control Button

Prior control buttons are capable of delivering the same amount of oxygen, for example 160 liters per minute, to the patient as the maximum flow "on demand." Recent studies have determined that high volume flow rates tend to force gas into the patient's stomach and can lead to other complications. It is anticipated that guidelines will soon be published, limiting the flow of oxygen delivered to a patient to 40 liters per minute or less. The control button in the above-mentioned Fabish patent also delivers oxygen until a pressure builds up behind a diaphragm which gradually forces the button back. This configuration causes the back pressure developed within the pressure chamber to remain constant, initially making it harder for a non-breathing patient to exhale and raise the exhalation diaphragm. In this instance, the resilient contraction of the patient's lung muscles can generate only a minimal force to lift the exhalation diaphragm against the pressure in the pressure chamber.

Figure 3A:
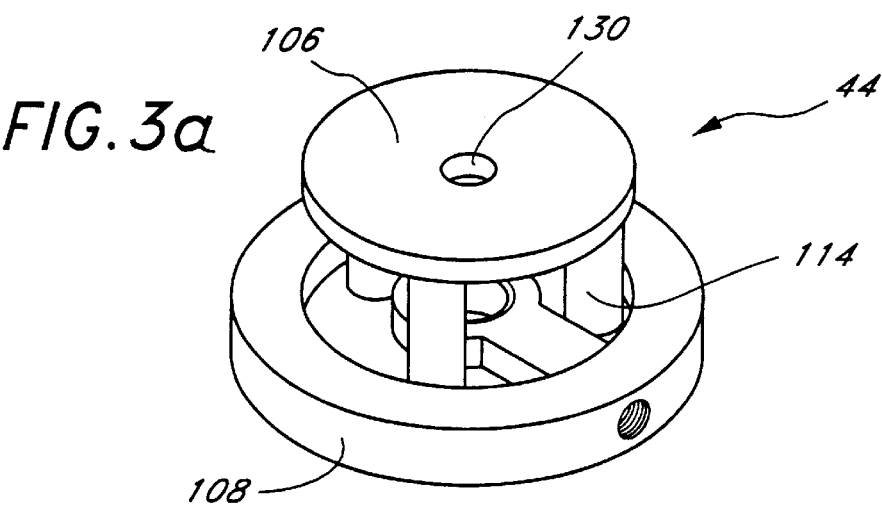
FIG. 3a is an assembled perspective view of the manual flow control button of the demand valve of FIG. 1.
Figure 3B:
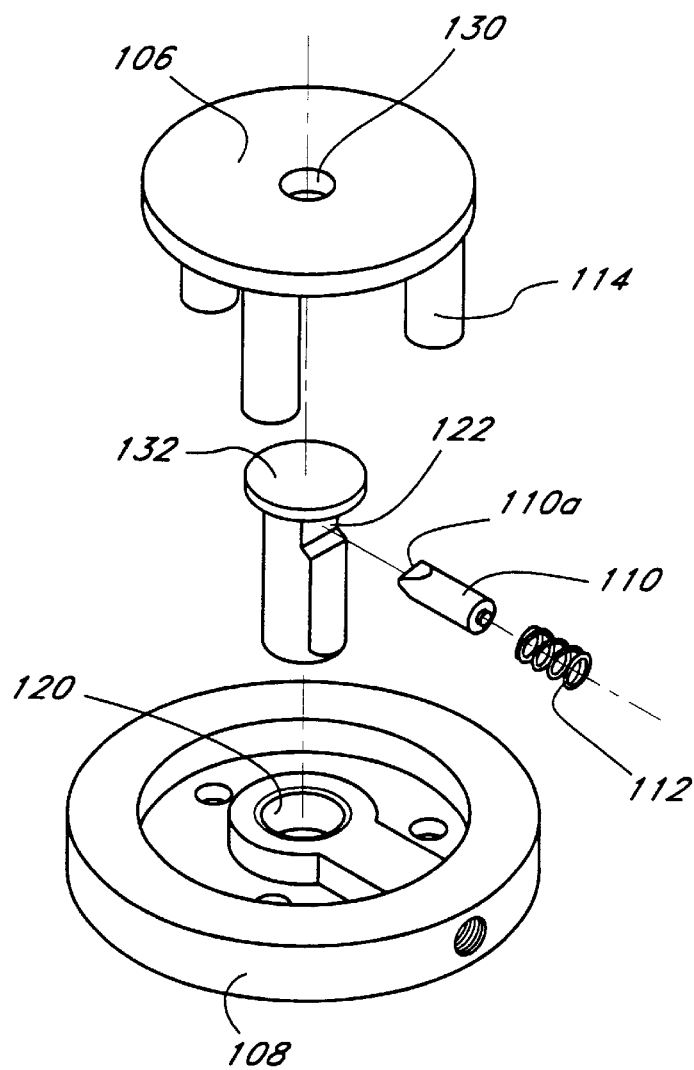

The control button 44 of the present invention is shown assembled and exploded in FIGS. 3a and 3b, respectively. The control button 44 comprises a thumb member 106 adapted to snap into a control disk 108, an actuating pin or shaft 80, a cam pin 110 and a cam spring 112. As seen also in FIG. 1, the thumb member 106 attaches to the control disk 108 by connecting legs 114 across a stop face 116. The stop face 116 partitions the control button body 43 into an outer recessed cup 115 which accommodates the travel of the thumb member 106 and an inner cylindrical cavity 117 in which the control disk 108 travels. The legs 114 slide within holes 118 in the stop face 116. The actuating shaft 80 inserts within a central bore 120 of the disk 108 and is held stationary therein by a detent comprising the cam pin 110 biased by the spring 112 into a notch 122. An angled tip 110a cooperates with the similarly angled notch 122 to provide the cam sliding surfaces. The cam pin 110 slides within a radially directed channel 111 in the control disk 108, the cam spring 112 acting between the rear of the pin and a backing plug or set screw (not shown) within the channel. A circular stop 132 on the upper end of the shaft 80 contacts the inner stop face 116. The stop 132 also prevents the shaft 80 from passing through the bore 120 of the control disk 108.

The thumb member 106, control disk 108, and shaft 80 travel together to cause the rounded lower end 80a of the shaft to act on the main diaphragm 48 which, in turn, contacts and pivots the valve needle 46 to open the flow of oxygen. Advantageously, the tip of the actuation shaft 80a, main diaphragm 48 and blunt tip 64 are in contact when the valve needle 46 resides along the intake axis 56 in a valve closed position. The slightest pressure on the thumb member 106 thus tilts the valve needle 46 to initiate oxygen flow. Any space between the shaft end 80a, diaphragm 48 and blunt tip 64 would detrimentally result in a "dead" response zone after pressing the control button 44 during which no oxygen would flow. Operators of resuscitators prefer to gauge the proper oxygen flow rate at all times and such a "dead zone" reduces the capacity to precisely administer small bursts of oxygen.

Depressing the control button 44 of the present invention completely, however, delivers only a portion of the maximum possible flow, typically 40 liters per minute. This is accomplished by calibrating the flow rate versus the angle of the valve needle 46, and thereafter limiting the maximum inward travel of the actuating shaft 80. A limiting set screw 128, threadably engaged in a through-hole 130 in the thumb-member 106, bottoms out on the stop face 116 when the thumb member is pressed, thus limiting the travel of the operatively connected shaft 80. Since the control button 44 can only cause the main diaphragm 48 to advance a portion of its total travel, the valve needle 46 is only pivoted a short distance to produce the preferred limited oxygen flow of 40 liters per minute. The reduced flow is considered safer when the patient is not breathing normally. The rate of flow during manual operation may be adjusted by advancing or retracting the limiting screw 128 relative to the thumb member 106.

When the patient does begin to breathe, however, the demand valve 20 may allow up to 120 liters of oxygen per minute to flow. The maximum flow rate depends on the distance the diaphragm 48 may travel and tilt the valve needle 46, among other things, and may be altered depending on the design criteria. A baffle plate 75 beneficially alters the oxygen flow characteristics allowing the patient to more easily draw 120 liters per minute, as will be described below. As the patient inhales, the main diaphragm 48 advances a travel distance commensurate with the suction generated and the valve needle 46 is further pivoted, opening the delivery port 54 wide. The increased flow is needed by the now normally breathing patient and provides for more rapid recovery. Of course, the patient easily shuts off the flow of oxygen by exhaling, the reduction of suction within the chamber 30 releasing the diaphragm 48 and allowing the spring 68 and oxygen pressure on the upstream side of needle head 50 to close the delivery valve 32.

In accordance with a main aspect of the invention, the control button 44 automatically releases when a predetermined pressure is exceeded within the chamber 30, such as when the patient's lungs are full. A space develops between the control disk 108 and stop face 116 when the thumb-member 106 is depressed. Sufficient pressure within the chamber 30 acts on the main diaphragm 48 to "pop" the actuating shaft 80 upward against the camming force of the pin 110. The cam pin 110 retracts out of the notch 122, and the actuating shaft 80 moves upward into the space between the disk 108 and stop face 116. The specific pressure in the chamber 30 required to force the cam pin 110 out of the notch 122 depends on the retaining force exerted by the cam spring 112 and also on the geometry of the interfacing cam surfaces; less pressure is required to overcome shallow angled cam surfaces. Preferably, the pressure within the chamber 30 necessary to cause the shaft 80 to retract is at least 60 cm of water (0.85 psi), and more preferably, the pressure within the chamber 30 is 70 cm of water (1.0 psi). However, whatever threshold pressure is chosen, the design of the cooperating cam surfaces 110a and 122 is such that no relative motion occurs prior to the tripping force being reached. Thus, the predetermined flow rate is delivered to the patient right up to the instant the manual control button 44 is tripped.

The main diaphragm 48 retreats upon tripping of the actuating shaft 80, due to the pressure from the chamber 30 side, allowing the needle valve 46 to return to its initial position whereupon the oxygen delivery port 54 is closed by the head 50. The operator feels the control button 44 being "tripped" due to the sudden impact of the stop 132 on the underside of the stop face 116 and because of the decrease in feedback pressure on the thumb member 106. There also is an audible click from the collision between the stop 132 and stop face 116 to notify the operator that either the patient's lungs are full or the patient has exhaled.

The paramedic must release the thumb-member 106, which is returned by a spring 124, to reset the control button 44 and deliver more oxygen manually. The return spring 124, centered over an inward extension 126 of the thumb member 106, biases the thumb member outward against the rigid stop face 116. Consequently, when thumb pressure is released, the return spring 124 resets the control button 44 by relocating the cam pin 110, disposed in the control disk 108, into the notch 122 in the actuating shaft 80.

When the control button 44 is "tripped" by a sufficient pressure in the chamber 30, the sudden retreat of the diaphragm 48 increases the volume in the pressure chamber 30, thus decreasing the pressure therein, as the inflow of oxygen has stopped. This sudden pressure loss make it easier for the exhalation diaphragm 100 to move, allowing the patient to exhale.

In a non-typical sequence of events, in which the patient's airway is blocked for example, the paramedic actuates the control button 44 to deliver oxygen to a patient, whereupon pressure builds up in the pressure chamber 30 until the main diaphragm 48 retracts. Since the oxygen flow has been stemmed, the retreating diaphragm 48 decreases the pressure within the chamber 30 allowing the patient to more easily raise the exhalation diaphragm 100 and exhale through the channels 102.

Oxygen Flow Baffle

Figure 5A:
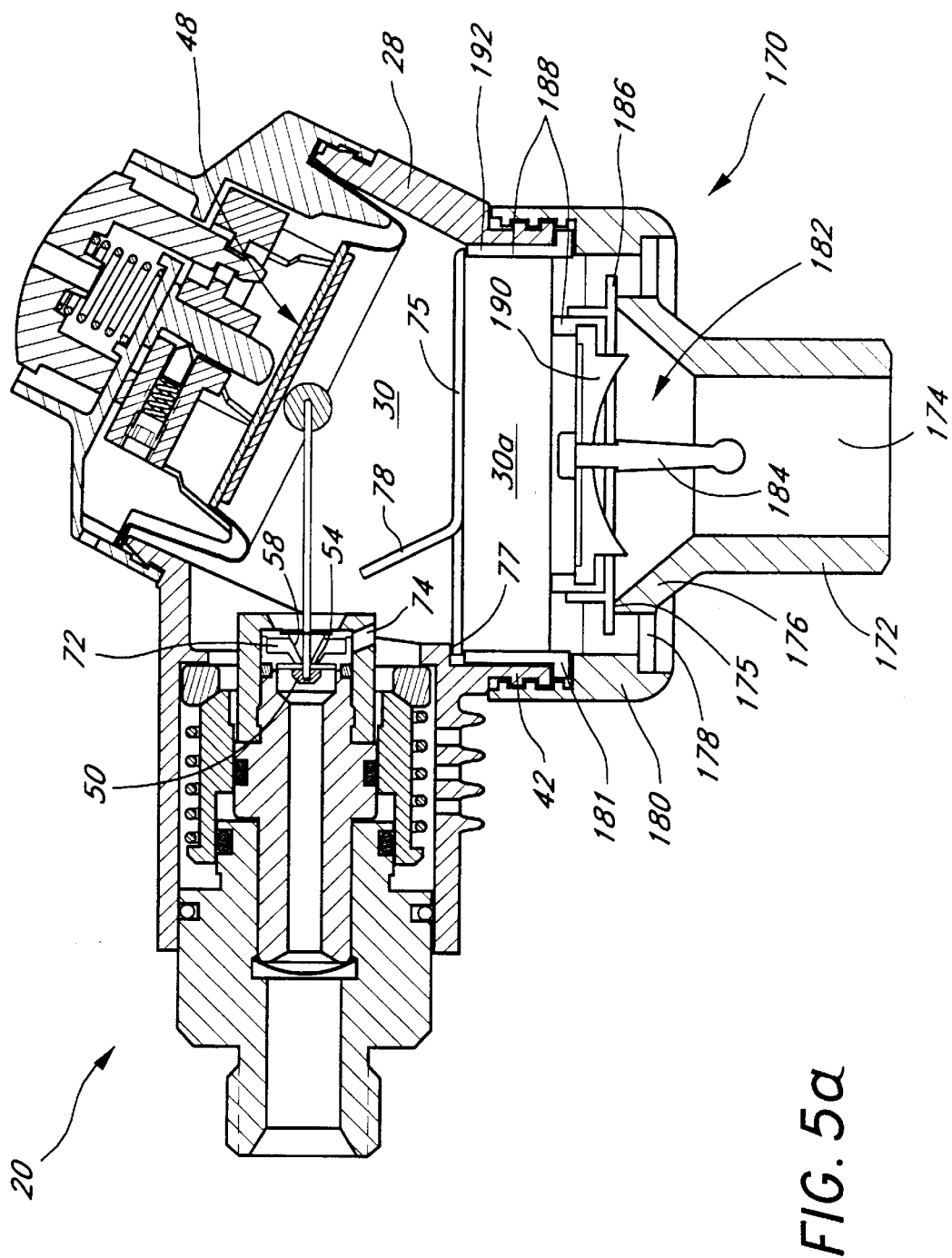
FIG. 5a is a cross-sectional view of the demand valve of the present invention with a preferred oxygen outlet configuration and showing an oxygen flow baffle.
Figure 5B:
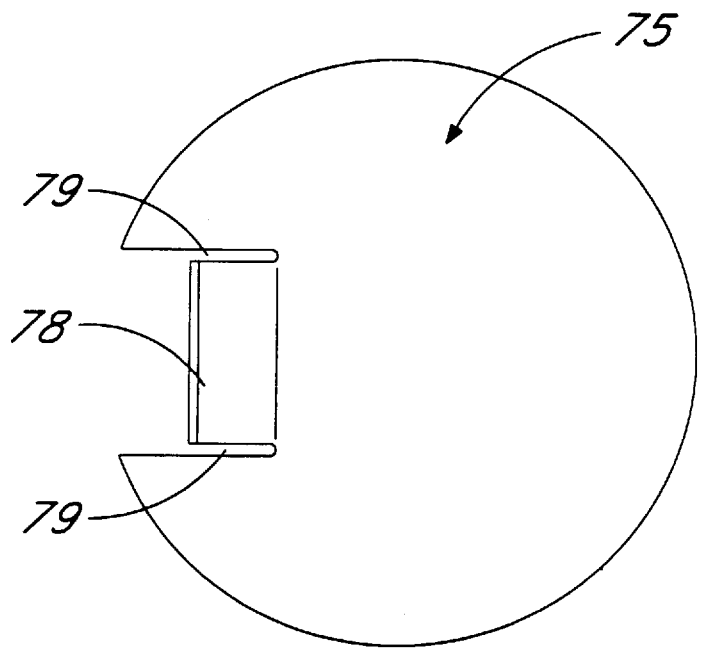
Figure 5C:
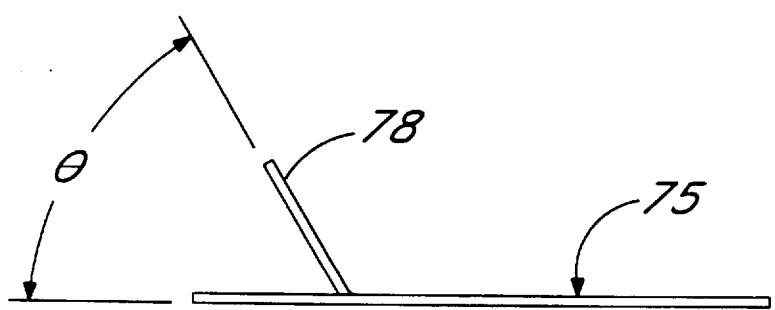
FIG. 5c is an elevational view of the baffle of FIG. 5b.

Referring now to FIGS. 5a–c, the oxygen flow passes around the head 50 and through the oxygen delivery port 54 into a deflection chamber 72. The conical deflector 58 forces the oxygen out of the deflection chamber 72 through an aperture 74 into the pressure chamber 30. The aperture 74 extends around a predetermined circumferential portion of the deflection chamber 72 so as to only exit at the lower side thereof as seen in FIG. 5a. The conical deflector 58 and deflection chamber 72 thus prevent oxygen from continuing straight through the oxygen delivery port 54 to impinge on the flexible main diaphragm 48 and force it back, thus affecting the diaphragm's position and oxygen flow rate.

Oxygen flow from the delivery port 54 through the pressure chamber 30 and to the patient is altered by a baffle plate 75 to create a beneficial pressure gradient across the plate. The baffle plate 75 extends across and covers the distal end of a tubular wall 192 of a flexible exhalation diaphragm and is partially engaged between the wall and an interior shoulder 77 of the demand valve housing 28. The plate 75 is generally circular except for a rectangular tab 78 formed by parallel slots 79 in one side, as seen in FIGS. 6b–c. The tab 78 preferably forms an angle θ with the plate 75 (preferably sixty degrees) toward the delivery valve 54. The tab directs oxygen to an outlet port 170.

During the delivery of oxygen through the aperture 74, the angle tab 78 acts as a flow diverter creating a pressure differential across the plate 75 between the main pressure chamber 30 and a lower chamber 30a. The high velocity expanding oxygen traveling through the hole in the baffle plate 75 acts like a venturi, or constricted throat, lowering the pressure above the plate. A reduced pressure in the main chamber 30 moves the main diaphragm 48 to tilt the valve stem 46 farther and allow the patient to receive the maximum flow rate with less effort. In order to modulate the beneficial pressure differential across the plate 75, a poor seal exists between the plate and the exhalation diaphragm wall 192 in those areas not firmly held by the shoulder 77 (e.g. at the right of the plate in FIG. 5a). The leakage modulates the pressure across the baffle plate 75 preventing the pressure differential from becoming too great.

Outlet Port

In a preferred embodiment, illustrated in FIGS. 5–9, an outlet port 170 comprises a cylindrical nozzle extension 172 through which a passageway 174 communicates with the pressure chamber 30. The passageway 174 terminates in a circular valve seat 175 at the innermost end of a cylindrical seat flange 176. Circumferentially spaced exhaust ports 178 are disposed between the nozzle extension 172 and an internally threaded outer extension 180. The extension 180 threadably engages the cylindrical outlet and traps an outwardly extending flange 181 of an exhalation valve assembly 182 therebetween to hold the assembly over the cylindrical seat flange 176.

The valve assembly 182 comprises a central pin 184 extending through and joining a valve seat cap 186, a flexible diaphragm 188 and a flapper valve seat 190. As seen in FIG. 5a, the exhalation valve 182 is positioned such that the valve seat cap 186 sealingly contacts the circular valve seat 175 and the tubular wall 192 of the flexible diaphragm 188 extends upwardly into the pressure chamber 30.

The exhalation valve 182 is shown assembled and in parts in FIGS. 6–9. The central pin 184, valve seat cap 186 and flapper valve seat 190 are preferably constructed of a rigid material such as polysulfone or polycarbonate. The flexible diaphragm 188 is preferably silicon rubber, to retain flexibility under temperature extremes. In general, the valve seat cap 186 and flapper valve seat 190 sandwich a central circular disk-shaped portion 193 of the diaphragm 188 therebetween with the valve seat cap to the side of the patient.

With reference to FIGS. 7a–b, the flapper valve seat 190 comprises an outer ring 198 having a circular projection ring 200 connected by four support legs 202. As seen best in FIG. 7b, the projection ring 200 transitions from the surface of the outer ring 198 along one center axis of the flapper valve seat 190 to a maximum height above the outer ring along a perpendicular center axis. Two of the support legs 202a therefor comprise an arcuate projecting surface while the other two legs 202b maintain a generally flat surface. A central circular bridge 204 joins the four legs 202 with a bore 206 therein for receiving the central pin 184.

As seen in FIGS. 8a–b, the flexible diaphragm 188 comprises the aforementioned wall portion 192 and central disk-shaped region 193 with a ring-shaped membrane 208 therebetween. A tubular retaining segment 210 joins the membrane 208 to a flapper valve support 212 extending across the tubular segment. Two thin flapper valves 214 integral with the support 212 extend across the two semi-circular apertures formed by the tubular segment 210 and support. The support 212 also includes a central circular region with a through-bore 216 sized to tightly receive the central pin 184.

Referring to FIGS. 9a–b, the valve seat cap 186 comprises a flat annular sealing ring 218 spanned by a bridge 220 having an enlarged central portion with a through-bore 222 for the central pin 184. A tubular wall 224 perpendicular to the sealing ring 218 is sized to extend over the central disk-shaped portion of the diaphragm 193.

With reference again to FIGS. 6a–b, the flapper valve seat 190 is retained in a notch 211 in the inner tubular segment 210 of the diaphragm such that the projecting ring 200 and legs 202a contact and displace the flappers 214. The contact of the flappers 214 to the flapper valve seat 190 forms a seal such that gas may only flow one-way from the pressure chamber 30 to the passageway 174. A larger pressure in the passageway 174 causes the flappers 214 to contact and seal to the valve seat 190. The arcuate configuration of the projecting ring 200 and legs 202a, and the resiliency of the flappers 214, maintains a good seal even when no pressure differential exists.

The exhalation valve seat cap 186 fits on the opposite side of the diaphragm 188 with the bridge 220 aligned over the flat legs 202b and the flapper support 212 so that the flappers 214 may extend through the semi-circular apertures within the annular sealing ring 218. The central pin 184 extends through the respective bores 206, 216, 222 to firmly hold the central components of the exhalation valve 182 together. The central disk-shaped region 193, flapper valve seat 190, central pin 184 and exhalation valve seat cap 186 may move in unison relative to the outer wall of the diaphragm 192 due to the flexibility of the membrane 208. As stated above, a pressure differential across the exhalation valve 182 from the patient exhaling shuts the flappers 214. The central components of the valve 182 are thus forced toward the pressure chamber 30 and the valve seat cap 186 disengages with the valve seat 175, allowing the patient to exhale through the ports 178, as seen in FIG. 5a. Ideally, the amount of pressure necessary to exhale must be just greater than ambient pressure so as to provide a minimal resistance to the patient.

In an alternative embodiment, shown in FIG. 1, the outlet port 34 comprises a cylindrical nozzle extension 82 through which a passageway 84 communicates with the pressure chamber 30. The passageway 84 terminates in a circular valve seat 86 at the innermost end of a cylindrical seat flange 88. A disk-shaped cap 90 mates with the valve seat 86 in an air-tight seal. The cap has an integral elastomeric skirt 91 extending from the periphery which is held in an air-tight manner between the housing of the demand valve 28 and an internally threaded outer extension 92 of the outlet port 34. The rigid cap 90 includes one or more apertures 94 through which oxygen may flow from the pressure chamber 30 through the passageway 84 and out the nozzle 82. A circular one-way flapper 36 affixed to a central pin 96 of the cap 90 sealably mates with a circular rib 98 on the outlet side of the cap to cover the apertures 94. The one-way flapper 36 is sufficiently flexible to allow oxygen to pass freely from the pressure chamber 30 through to the passageway 84 with a minimum of resistance. On the other hand, the flapper 36 provides a minimum of rigidity to sealingly cover the apertures 94 and prevent air from entering the pressure chamber 30 from the nozzle side.

The combination of the cap 90, elastomeric skirt 91 and flapper 36 comprise an exhalation diaphragm 100. When the pressure within the passageway 84 reaches a predetermined value, the exhalation diaphragm 100 is forced upward off of the valve seat 86 due to the flexibility of the elastomeric skirt 91. This situation occurs when the patient exhales, the breath thus exhausting out through exhaust channels 102 in the outlet port 34.

Oxygen Intake Assembly

In some instances, the patient may be attached to a resuscitator without a source of oxygen connected. Such a dangerous situation may occur, for example, through negligence, or when an oxygen bottle runs out. An advantageous feature of the intake assembly 24 of the present invention allows the patient to instantly breath ambient air when no source of oxygen is connected.

Figure 10B:
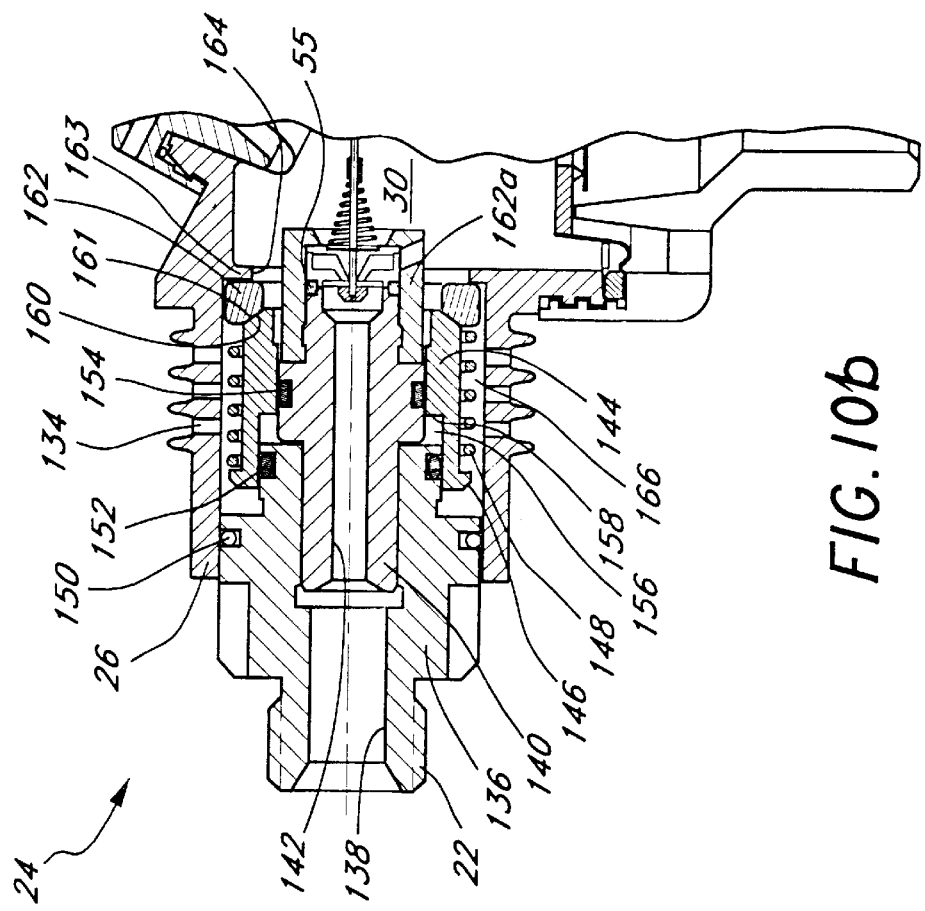
FIG. 10b is a partial cross-sectional view of the oxygen intake assembly.
Figure 10A:
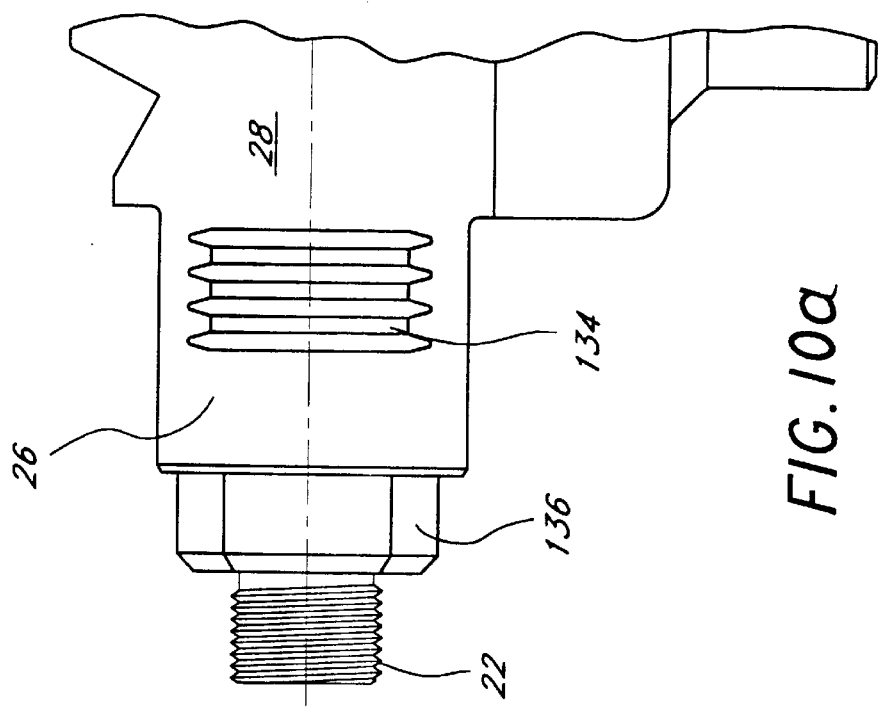

As seen best in FIGS. 10a–b, the housing 28 of the demand valve 20 includes air vents 134 along the oxygen inlet flange or conduit 26. The oxygen intake assembly 24 comprises a tubular fitting 136 having a central oxygen passageway 138, a tubular guide 140 also having an internal passageway 142 for oxygen and partially extending within the first tubular member, and a cylindrical sleeve or anti-suffocation valve member 144 arranged to slide longitudinally over the junction of the fitting 136 and the guide 140. Two elastomeric O-rings 152, 154 provide seals between the fitting 136 and valve member 144, and between the tubular guide 140 and the sleeve member, respectively.

The member 144 includes on one end an outwardly extending flange 146 which abuts a compression spring 148 arranged concentrically around the valve member. The other end of the spring engages a circular valve seat ring 162, urging it into engagement with an inwardly extending housing flange 163. The ring 162 is connected by spaced struts, forming anti-suffocation ducts 164, to a central tubular portion 162a. The tubular portion 162a forms the supporting structure of the oxygen delivery valve 32, referred to above. More specifically, the valve seat 53 of FIG. 2 forms the inner periphery of the portion 162a. The central tubular portion 162a is threadably connected to the inner end of the tubular guide 140 capturing the delivery valve 32 therebetween. An elastomeric sealing ring 55 is compressed between the tubular guide 140 and the valve seat 53 to prevent the escape of oxygen.

The oxygen intake assembly 24 inserts within the conduit 26 of the demand valve housing 28 and is held in place with a retaining clip 150. The clip 150 may be removed, and the entire assembly 24 may be detached from the demand valve 20. The assembly 24 may be independently tested for flow rate, leaks and performance of the anti-suffocation means before insertion into the demand valve 20.

Advantageously, the first tube 136, including the intake fitting 22, may swivel relative to the demand valve 20. This allows the demand valve 20 to orient itself with respect to stiff oxygen hoses which has proved to be a problem in the past. The decoupled structure between the intake fitting 22 and delivery valve 32 allows the fitting to rotate without affecting the delivery valve or valve needle 46. Furthermore, the intake fitting 22 may be rotated without altering the preferred orientation of the oxygen flow aperture 74 toward the angled tab 78 of the baffle plate 75 providing beneficial flow characteristics.

The vents 134 open into an annular recess 166 in which the spring 148 acts against the flange 146 to bias the valve member 144 to the left. The valve member 144 includes a beveled valve face 160 shaped to sealingly mate with the valve seat 161 on the valve seat ring 162 disposed at the inner end of the annular recess 166. In the absence of an oxygen supply, the spring 148 urges the valve member 144 to a valve open position with respect to the valve seat 161 and the vents may communicate with the pressure chamber 30 via anti-suffocation ducts 164. When oxygen is supplied, the pressure urges the anti-suffocation valve member 144 closed against the seat 161, preventing communication between the vents 134 and the pressure chamber 30.

A certain annular tolerance is left between the fitting 136 and the guide 140 so that oxygen pressure is applied to an annular space 156 between the tubular guide and the anti-suffocation valve member 144. When oxygen is supplied to the intake fitting 22, the pressure within the annular space 156 acts on an interior shoulder 158 of the member 144 to force the member to the right against the bias of the spring 148, as seen in FIG. 10b. When the oxygen is depleted, the spring 148 moves the valve member 144 to the left, separating the member from the valve seat ring 162 to open the valve and provide an air pathway through the vents 134, recess 166, and ducts 164 in the housing 28 to the pressure chamber 30. The spring 148 is selected to force the valve member 144 to the left to open the valve at a predetermined reduced oxygen inlet pressure, less than such pressure being considered deleterious to the patient. Thereafter, the patient only has to overcome the flapper 36 or flappers 214 to breathe in.

In certain embodiments of the demand valve of the present invention, a pressure relief valve (not shown) is included in the wall of the pressure chamber 30. Such a relief valve prevents the buildup of internal pressure in the demand valve 20 above a predetermined value. The pressure relief valve is a simple check valve which opens to exhaust gas out of the pressure chamber in event of a pressure buildup.

The demand valve 20 may be used in a CPR procedure in conjunction with repetitive pressure of the patient's chest, or may be used by itself in cases when the heart is still beating. The demand valve 20 is coupled to a source of oxygen and the breathing mask fitted over a patient. The paramedic delivers intermittent bursts of oxygen by manually pressing the control button 44, or the patient breathes through the valve 20 without assistance. The outlet port 34 allows for exhalation of the patient by the upward movement of the exhalation diaphragm 100.

What is claimed is:

1. A resuscitator for supplying breathing gas to a patient, comprising:
   a housing having a pressure chamber with a breathing gas inlet and a breathing gas outlet for directing gas from the chamber to a patient;
   a moveable element connected to the housing in a manner to move in response to pressure changes in said chamber;
   a normally closed valve in said inlet controlling the flow of breathing gas into the chamber, said valve being connected to said element to open in response to movement of said element as a result of a reduction in pressure in said chamber caused by a patient's inhalation demand for breathing gas through said gas outlet;
   a manually controlled actuator mounted on said housing to apply a force to said pressure responsive element to cause said element to move and open said valve; and
   said actuator including structure which is responsive to a predetermined threshold pressure in said chamber applied to said element to become temporarily unable to apply any force to said element.

2. The resuscitator of claim 1, including means for limiting movement of said actuator that will open said valve to provide less than half that gas flow which can be caused by patient demand.

3. The resuscitator of claim 2, wherein said limiting means is sized so that said actuator can only cause said valve to provide about one-third of the flow that the valve can provide in response to patient demand.

4. The resuscitator of claim 1, wherein said actuator includes an adjustable limiting device for limiting the opening of said valve to provide an adjustable fraction of that gas flow which can be caused by patient demand.

5. The resuscitator of claim 1, wherein said valve includes a slender elongated valve stem that extends into said chamber, said element being positioned close to a free end of said valve stem and being oriented such that a reduction in pressure in said chamber caused by the patient demanding breathing gas will cause said element to move said valve stem so as to open said valve.

6. The resuscitator of claim 5, wherein said actuator moves said element in a direction to move the end of said valve stem so as to open said valve.

7. The resuscitator of claim 5, wherein said actuator includes a pin positioned to push said element towards the valve stem, and a manually operated control button connected to said actuator pin by a releasable detent, said detent being constructed to disable the connection between the actuator pin and the push button upon application of a retracting force on said pin by said element as a result of a predetermined pressure level in said chamber.

8. The resuscitator of claim 7, wherein said detent includes a spring-loaded pin having an angled tip which mates with a mating angled surface on the side of said actuator pin, and said detent pin is connected to move with said push button such that when said push button is depressed, said detent pin moves said actuator pin in a direction to move said element.

9. The resuscitator of claim 7, wherein said actuator pin can retract in response to a predetermined force causing said detent pin to retract so that it no longer connects the actuator pin to said push button, thereby allowing the actuator pin and said pressure responsive element to be retracted in response to increased pressure within said chamber.

10. The resuscitator of claim 1, including a conduit in a wall of said housing having one end opening into said chamber and another end adapted to be connected to a patient's breathing mask, an exhaust valve member covering the end of said conduit opening to said chamber, a flexible diaphragm connected to said housing and carrying said exhaust valve member, said diaphragm permitting said exhaust valve member to be moved away from the end of said conduit in response to patient exhalation pressure to permit a patient to exhale through said conduit, said housing including an opening to atmosphere that is in communication with said conduit when said exhaust valve member is moved away from the end of said conduit.

11. The resuscitator of claim 10, including an opening in said exhaust valve member for permitting breathing gas to flow from said chamber through said conduit to the patient, a one-way valve element mounted on said exhaust valve member that permits gas flow from said chamber through the opening in said exhaust valve member with a very slight pressure differential, but prevents patient exhalation gas flow from said conduit into said chamber.

12. A resuscitator for supplying breathing gas to a patient, comprising:
    a housing having a pressure chamber with a breathing gas inlet and a breathing gas outlet for directing gas from the chamber to a patient;
    an element moveable in response to pressure in said chamber;
    a normally closed valve in said inlet for controlling the flow of breathing gas into the chamber, said valve being moveable into an element to open position in response to movement of said element as a result of negative pressure in said chamber caused by a patient's inhalation demand for breathing gas;
    a manually controlled actuator which can apply a force to said pressure responsive element to cause said element to move and open said valve; and
    said actuator being responsive to a predetermined threshold pressure in said chamber applied to said element to become temporarily unable to apply said force;
    said actuator includes a push button positioned on one side of a partition, a plurality of spaced legs connected to said push button and extending through said partition, a control disk connected to said legs, an actuator pin positioned within a central opening of said control disk, a spring loaded detent mounted in said control disk having its radially inner end urged into driving engagement with said pin and a spring urging said push button into an undepressed position and thereby urging said control disk towards said partition, said push button together with said control disk and actuator pin being depressible to move said pressure responsive element to open said valve, said actuator pin being spaced from said partition with said push button in its depressed condition so that an increase of pressure within said chamber beyond a predetermined maximum will cause said actuator pin to be pushed towards said partition disconnecting it from said detent pin with said push button still depressed.

13. The resuscitator of claim 12, wherein said detent pin is reconnectable with said actuator pin when the push button is manually released and moved with said control disk to an undepressed condition by said push button spring.

14. Apparatus for supplying oxygen to a patient, either in response to a patient's inhalation negative pressure or in response to manual control by an attendant, said apparatus comprising:
    a pressure chamber including a flexible diaphragm that moves in response to the pressure in the chamber;
    a valve controlling the flow of oxygen into the chamber, said valve being moveable into an open position in response to movement of said diaphragm as a result of reduced pressure in said chamber caused by a patient's inhalation; and
    a manually controlled actuator assembly positioned to move said diaphragm in a manner to open said valve, said assembly including a manually operated control element and a connection for transmitting an actuating force between said element and said diaphragm, said connection being constructed to become automatically disconnected in response to a predetermined threshold pressure in said chamber applied to said diaphragm and thereby becoming unable to transmit sufficient force to said diaphragm to open said valve;
    wherein said connection employs a detent arrangement which becomes disconnected when the manually operated control element is being manually depressed and the diaphragm is subjected to said threshold pressure, said detent arrangement being restored to operative condition upon release of said manually operated control element.

15. A resuscitator for supplying breathing gas to a patient, comprising:
    a housing having a pressure chamber with a breathing gas inlet and a breathing gas outlet for directing gas from the chamber to a patient;
    a moveable element connected to the housing in a manner to move in response to pressure changes in said chamber;
    a normally closed valve in said inlet controlling the flow of breathing gas into the chamber, said valve being connected to said element to open in response to movement of said element as a result of a reduction in pressure in said chamber caused by a patient's inhalation demand for breathing gas through said gas outlet;
    a manually controlled actuator mounted on said housing to apply a force to said pressure responsive element to cause said element to move and open said valve; and
    said actuator including structure which automatically reduces pressure on said element responsive to a predetermined threshold pressure in said chamber applied to said element.

16. The resuscitator of claim 15, wherein said actuator includes an adjustable limiting device for limiting the opening of said valve to provide an adjustable fraction of that gas flow which can be caused by patient demand.

17. The resuscitator of claim 15, wherein said valve includes a slender elongated valve stem that extends into said chamber, said element being positioned close to a free end of said valve stem and being oriented such that a reduction in pressure in said chamber caused by the patient demanding breathing gas will cause said element to move said valve stem so as to open said valve.

18. The resuscitator of claim 17, wherein said actuator includes a pin positioned to push said element towards the valve stem, and a manually operated control button connected to said actuator pin by a releasable detent, said detent being constructed to disable the connection between the actuator pin and the push button upon application of a retracting force on said pin by said element as a result of a predetermined pressure level in said chamber.

* * * * *